United States Patent
Jalota et al.

(10) Patent No.: US 9,101,665 B2
(45) Date of Patent: *Aug. 11, 2015

(54) RAPID SETTING HIGH STRENGTH CALCIUM PHOSPHATE CEMENTS COMPRISING CYCLODEXTRINS

(71) Applicant: Skeletal Kinetics, LLC, Cupertino, CA (US)

(72) Inventors: Sahil Jalota, Santa Clara, CA (US); David C. Delaney, Capitola, CA (US); Duran N. Yetkinler, San Jose, CA (US)

(73) Assignee: Skeletal Kinetics, LLC, Cupertino, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/163,988

(22) Filed: Jan. 24, 2014

(65) Prior Publication Data

US 2014/0202359 A1 Jul. 24, 2014

Related U.S. Application Data

(63) Continuation of application No. 12/568,531, filed on Sep. 28, 2009, now Pat. No. 8,673,364.

(51) Int. Cl.
- *A61K 47/26* (2006.01)
- *C04B 12/02* (2006.01)
- *C04B 28/34* (2006.01)
- *C04B 111/00* (2006.01)

(52) U.S. Cl.
CPC ............... *A61K 47/26* (2013.01); *C04B 12/02* (2013.01); *C04B 28/344* (2013.01); *A61L 2400/10* (2013.01); *C04B 2111/00836* (2013.01)

(58) Field of Classification Search
CPC ...................................................... C04B 12/02
USPC ........................... 424/602, 489; 106/690, 691
See application file for complete search history.

(56) References Cited

U.S. PATENT DOCUMENTS

| | | | |
|---|---|---|---|
| 2,735,823 A | 2/1956 | Barrett | |
| 4,859,383 A | 8/1989 | Dillon | |
| 5,032,552 A | 7/1991 | Nonami et al. | |
| 5,679,294 A | 10/1997 | Umezu et al. | |
| 5,683,667 A | 11/1997 | Fulmer et al. | |
| 5,939,039 A | 8/1999 | Sapieszko et al. | |
| 5,968,253 A | 10/1999 | Poser et al. | |
| 5,997,624 A | 12/1999 | Chow et al. | |
| 6,206,957 B1* | 3/2001 | Driessens et al. | 106/35 |
| 6,334,891 B1 | 1/2002 | Constantz et al. | |
| 6,558,709 B2 | 5/2003 | Higham | |
| 6,719,993 B2 | 4/2004 | Constantz | |
| 7,175,858 B2 | 2/2007 | Constantz et al. | |
| 7,223,420 B2 | 5/2007 | Berger et al. | |
| 7,252,672 B2 | 8/2007 | Yetkinler et al. | |
| 7,252,833 B2 | 8/2007 | Constantz et al. | |
| 7,252,841 B2 | 8/2007 | Constantz et al. | |
| 7,261,717 B2 | 8/2007 | Yetkinler et al. | |
| 7,261,718 B2 | 8/2007 | Constantz et al. | |
| 7,294,187 B2 | 11/2007 | Chow et al. | |
| 7,306,786 B2 | 12/2007 | Delaney et al. | |
| 7,416,602 B2 | 8/2008 | Murphy et al. | |
| 7,527,687 B2 | 5/2009 | Genge et al. | |
| 7,892,346 B2 | 2/2011 | Insley et al. | |
| 7,892,347 B2 | 2/2011 | Insley et al. | |
| 2001/0021389 A1 | 9/2001 | Starling et al. | |
| 2003/0049329 A1 | 3/2003 | Lee et al. | |
| 2004/0005592 A1 | 1/2004 | Emtage et al. | |
| 2004/0029699 A1 | 2/2004 | Lemaitre et al. | |
| 2004/0250730 A1 | 12/2004 | Delaney et al. | |
| 2005/0009176 A1 | 1/2005 | Constantz | |
| 2005/0058717 A1 | 3/2005 | Yetkinler et al. | |
| 2005/0249813 A1 | 11/2005 | Hendricks et al. | |
| 2005/0260278 A1 | 11/2005 | Constantz et al. | |
| 2006/0018974 A1* | 1/2006 | Constantz et al. | 424/603 |
| 2006/0213398 A1 | 9/2006 | Barralet et al. | |
| 2006/0225621 A1 | 10/2006 | Insley et al. | |
| 2006/0292200 A1 | 12/2006 | Delaney | |
| 2007/0128245 A1 | 6/2007 | Rosenberg et al. | |
| 2007/0189951 A1 | 8/2007 | Constantz et al. | |
| 2008/0028992 A1 | 2/2008 | Lee et al. | |

(Continued)

FOREIGN PATENT DOCUMENTS

| | | | |
|---|---|---|---|
| EP | 0950420 | A2 | 10/1999 |
| WO | WO 01/82834 | A1 | 11/2001 |
| WO | WO 2007/124511 | A2 | 11/2007 |

OTHER PUBLICATIONS

Kong et al., "Phase Conversion of Tricalcium Phosphate Into Ca-Deficient Apatite During Sintering of Hydroxyapatite-Tricalcium Phosphate Biphasic Ceramics", Journal of Biomedical Materials Research Part B: Applied Biomaterials, pp. 334-339 (2007).

Mostafa, Nasser Y., "Characterization, thermal stability and sintering of hydroxyapatite powders prepared by different routes", Materials Chemistry and Physics, vol. 94, pp. 333-341 (2005).

Takagi, et al., "Formation of hydroxyapatite in new calcium phosphate cements", Biomaterials. Sep. 1998; 19(17): 1593-9.

Thangamani, et al., "The effect of powder processing on densification, microstructure and mechanical properties of hydroxyapatite", Ceramics International, 28, 2002, pp. 355-362.

(Continued)

*Primary Examiner* — Kaj K Olsen
*Assistant Examiner* — Karam Hijji
(74) *Attorney, Agent, or Firm* — Bret E. Field; Bozicevic, Field & Francis LLP

(57) ABSTRACT

Rapid setting high strength calcium phosphate cements and methods of using the same are provided. Aspects of the cements include fine and coarse calcium phosphate particulate reactants and a cyclodextrin which, upon combination with a setting fluid, produce a flowable composition that rapidly sets into a high strength product. The flowable compositions find use in a variety of different applications, including the repair of hard tissue defects, e.g., bone defects such as fractures.

3 Claims, 1 Drawing Sheet

(56) References Cited

U.S. PATENT DOCUMENTS

2010/0249794 A1    9/2010    Moseley et al.
2010/0269736 A1    10/2010    Chow et al.
2011/0073006 A1    3/2011    Jalota et al.

OTHER PUBLICATIONS

Wang, et al., "Sintering behaviour and mechanical properties of hydroxyapatite and dicalcium phosphate", Journal of Materials Science Materials in Medicine, 1993, 4, pp. 150-158.

* cited by examiner

RAPID SETTING HIGH STRENGTH CALCIUM PHOSPHATE CEMENTS COMPRISING CYCLODEXTRINS

INTRODUCTION

Calcium phosphate cements find use as structural materials in the orthopedic and dental fields. Such cements are typically prepared by combining a dry component(s) and a liquid to form a flowable paste-like material that is subsequently capable of setting into a solid calcium phosphate product. Materials that set into solid calcium phosphate mineral products are of particular interest as such products can closely resemble the mineral phase of natural bone and are susceptible to remodeling, making such products extremely attractive for use in orthopedics and related fields.

While a large number of different calcium phosphate cement formulations have been developed, there is a continued need for the development of yet more advanced formulations.

SUMMARY

Rapid setting high strength calcium phosphate cements and methods of using the same are provided. Aspects of the cements include fine and coarse calcium phosphate particulate reactants and a cyclodextrin which, upon combination with a setting fluid, produce a flowable composition that rapidly sets into a high strength product. The flowable compositions find use in a variety of different applications, including the repair of hard tissue defects, e.g., bone defects such as fractures.

DETAILED DESCRIPTION

Figure 1A:
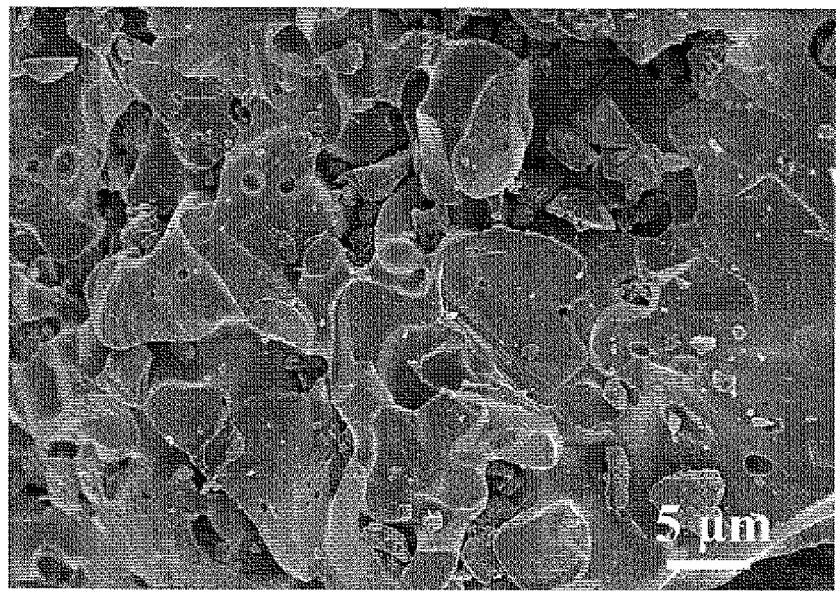
FIG. 1a shows an SEM micrograph of particles that are 38-106 μm.

Rapid setting high strength calcium phosphate cements and methods of using the same are provided. Aspects of the cements include fine and coarse calcium phosphate particulate reactants and a cyclodextrin which, upon combination with a setting fluid, produce a flowable composition that rapidly sets into a high strength product. The flowable compositions find use in a variety of different applications, including the repair of hard tissue defects, e.g., bone defects such as fractures.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Methods recited herein may be carried out in any order of the recited events which is logically possible, as well as the recited order of events.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

All publications mentioned herein are incorporated herein by reference to disclose and describe the methods and/or materials in connection with which the publications are cited.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Calcium Phosphate Cements and Methods of Using the Same

As summarized above, aspects of the invention include rapid setting high strength calcium phosphate cements. As the cements are rapid setting high strength calcium phosphate cements, upon combination of the dry component of the cement with a setting fluid, a flowable composition is produced which sets into a solid product that rapidly sets into a high strength product, as described in greater detail below.

Aspects of calcium phosphate cements of embodiments of the invention include a dry reactant component that includes the presence of a first fine particulate calcium phosphate reactant having a mean particle size of 8 μm or less; and a second coarse calcium phosphate reactant having a mean particle size that is 10 μm or greater.

The fine particulate calcium phosphate reactant is a calcium and/or phosphate dry reactant, e.g., a calcium phosphate mineral, having a mean particle size (as determined using the Horiba LA-300 laser diffraction particle sizer (Version 3.30 software for Windows 95) (Irvine, Calif.)) of 8 μm or less and a narrow particle size distribution. The mean particle size of this fine particle reactant may vary, ranging in certain embodiments from 1 to 7 μm, such as from 1 to 6 μm, including from 1 to 5 μm, where the mean particle size of the fine particle reactant in certain embodiments may be 1, 2, 3 and 4 μm, where in certain embodiments the mean particle size is 3 μm. The fine particle reactant is further characterized by having a narrow particle size distribution. By narrow particle size distribution is meant that the standard deviation of the particles that make up the fine particle reactant (as determined using the Horiba LA-300 laser diffraction particle sizer (Version 3.30 software for Windows 95) (Irvine, Calif.)) is 4.0 μm or less, and in certain embodiments is 3.0 μm or less, e.g., 2.5 μm or less, including 2.0 μm or less. The fine particulate reactant is further characterized in that the mode (as determined using the Horiba LA-300 laser diffraction particle sizer (Version 3.30 software for Windows 95) (Irvine, Calif.)) is 8.0 μm or less, and in certain embodiments 6.0 μm or less, e.g., 5 μm or less, including 3.0 μm or less. In certain embodiments, the fine particulate reactant is a calcium phosphate compound having a calcium to phosphate ratio ranging from 1.0 to 2.0, including from 1.33 to 1.67, such as 1.5. Calcium phosphates of interest include include: MCPM (monocalcium phosphate monohydrate or $Ca(H_2PO_4)_2 \cdot H_2O$); DCPD (dicalcium phosphate dihydrate, brushite or $CaHPO_4 \cdot 2H_2O$), ACP (amorphous calcium phosphate or $Ca_3(PO_4)_2 H_2O$), DCP (dicalcium phosphate, monetite or $CaHPO_4$), tricalcium phosphate, including both α- and β-$(Ca_3(PO_4)_2$, tetracalcium phosphate $(Ca_4(PO_4)_2O$, etc. In certain embodiments, the calcium phosphate compound is a tricalcium phosphate, such as α- and β-tricalcium phosphate, where in certain embodiments, the tricalcium phosphate is α-tricalcium phosphate.

Also present in the dry reactant component is a second coarse calcium phosphate reactant having a mean particle size that is 10 μm or greater. In certain embodiments, the particle size of this second reactant is 20 μm or greater, such as 25 μm or greater, including 30 μm or greater (as determined using the Horiba LA-300 laser diffraction particle sizer (Version 3.30 software for Windows 95) (Irvine, Calif.)), such as 50 μm or greater, 100 μm or greater, 150 μm or greater, including 200 μm or greater, where the particle size of this second reactant may range from 10 to 500 μm, such as from 25 to 250 μm. Calcium phosphates of interest include: MCPM (monocalcium phosphate monohydrate or $Ca(H_2PO_4)_2 \cdot H_2O$); DCPD (dicalcium phosphate dihydrate, brushite or $CaHPO_4 \cdot 2H_2O$), ACP (amorphous calcium phosphate or $Ca_3(PO_4)_2 H_2O$), DCP (dicalcium phosphate, monetite or $CaHPO_4$), tricalcium phosphate, including both α- and β-$(Ca_3(PO_4)_2$, tetracalcium phosphate $(Ca_4(PO_4)_2O$, etc. In certain embodiments, the calcium phosphate compound is a tricalcium phosphate, such as α- and β-tricalcium phosphate.

In certain embodiments, the second coarse particle calcium phosphate reactant is α-tricalcium phosphate. In these embodiments, the dry reactants include a tricalcium phosphate coarse particle composition that has mean particle size that is at least 2 times larger than the mean particle size of the fine particles component, where the mean particle size of coarse particle component may be 20 μm or larger, 30 μm or larger, 40 μm or larger (as determined using the Horiba LA-300 laser diffraction particle sizer (Version 3.30 software for Windows 95) (Irvine, Calif.)), such as 50 μm or larger, 100 μm or larger, 150 μm or larger, 200 μm or larger, where the particle size of the tricalcium phosphate coarse particle component population (also referred to herein as a coarse particle size population) may range from 10 to 500 μm, such as from 25 to 250 μm. In certain instances, the particles of this component can range in size from 38 μm to 212 μm, such as from 38 μm to 106 μm or 106 μm to 212 μm. In some instances, the coarse particle reactant is produced by the methods described in U.S. patent application Ser. No. 12/328,720; the disclosure of which is herein incorporated by reference.

In certain embodiments, the amount of the fine particle reactant in the dry reactant component is greater than the total amount of other reactants that may be present in the dry reactant component, such as the coarse particle reactant as described herein. In these embodiments, the mass ratio of the fine particle reactant to the total mass of the dry reactants of the dry reactant component may range from 1 to 10, e.g., from 9 to 6, such as from 9 to 7, including from 9.5 to 8.5.

The ratios or relative amounts of each of the disparate fine and coarse particle reactants in the dry reactant component is one that provides for the desired calcium phosphate product upon combination of the dry reactant component with the setting fluid and subsequent setting. In certain embodiments, the overall ratio of all of the disparate calcium and/or phosphate compounds in the dry reactants in terms of the calcium to phosphate ration in the dry reactant component ranges from 4:1 to 0.5:1, usually from 2:1 to 1:1 and more usually from 1.9:1 to 1.33:1.

The fine and coarse particle reactants may be made up of the same or different compounds, e.g., the same or different calcium minerals, such as the same or different calcium phosphate minerals. For example, in certain embodiments of interest, the dry reactant component includes both coarse and fine particles of the same calcium containing mineral, e.g., α-tricalcium phosphate. In yet other embodiments, a portion, if not all of the coarse population of particles is made up of one or more different calcium containing compounds as compared to the compound making up the fine particle size population. For example, in certain embodiments, one may have a fine particle reactant made up of a first calcium containing compound, e.g., α-tricalcium phosphate particles, and a coarse particle reactant made up of a second calcium containing compound that differs in some way from the compound making up the first population, e.g., in terms of phase, molecular formula, solubility, radiopacity, etc. In certain embodiments, the fine and coarse particle reactants will be made up of different phases of the same calcium containing compound, such as the same calcium phosphate containing compound. For example, the coarse and fine particle size reactants could both be made up of tricalcium phosphate, but the fine particle reactant could be made up of α-tricalcium phosphate while the coarse particle reactant is made up of β-tricalcium phosphate particles, such that while the fine and coarse particle reactants are made up of the same compound, they are made up of different phases of the same compound, where the different phases differ from each other at least in terms of solubility. In yet other embodiments, the different reactants may be made up of different compounds, e.g., that differ from each other in terms of molecular formula, radiopacity, solubility, combinations thereof, etc. For example, in certain embodiments the fine particle reactant is made up of α-tricalcium phosphate particles, and a coarse particle reactant is made up at least partially of a different calcium containing compound, e.g., that differs in terms of at least molecular formula, if not radiopacity. For example, the coarse particle reactant may include a calcium containing compound that is not a tricalcium phosphate, such as in those embodiments where the coarse particle reactant is made up of a combination of β-tricalcium phosphate particles and particles of dolomite ($CaMgCO_3$).

During use, the cement dry reactant component is combined with a setting fluid. Setting fluids of interest vary, and include a variety of physiologically compatible fluids, including, but not limited to: water (including purified forms thereof), aqueous alkanol or polyol solutions, e.g., glycerol, where the alkanol or polyol is present in minor amounts, such as less than 20 volume percent; pH buffered or non-buffered solutions; solutions of an alkali metal hydroxide, acetate, phosphate or carbonate, particularly sodium, more particularly sodium phosphate or carbonate, e.g., at a concentration in the range of 0.01 to 2M, such as from 0.05 to 0.5M, and at a pH in the range of 6 to 11, such as from 7 to 9, including from 7 to 7.5; and the like.

In some instances, the dry reactant components are combined with a silicate setting fluid, i.e., a setting fluid that is a solution of a soluble silicate. By solution of a soluble silicate is meant an aqueous solution in which a silicate compound is dissolved and/or suspended. The silicate compound may be any compound that is physiologically compatible and is soluble in water. By soluble in water is meant a concentration of 1% or greater, 2% or greater and 5% or greater, where the concentration of the silicate employed typically ranges from 0-0.1 to 20%, usually from 0.01-5 to 15% and more usually from 5 to 10%.

Silicates of interest include, but are not limited to: sodium silicates, potassium silicates, borosilicates, magnesium silicates, aluminum silicates, zirconium silicates, potassium aluminum silicates, magnesium aluminum silicates, sodium aluminum silicates, sodium methylsilicates, potassium methylsilicates, sodium butylsilicates, sodium propylsilicates, lithium propylsilicates, triethanol ammonium silicates, tetramethanolamine silicates, zinc hexafluorosilicate, ammonium hexafluorosilicate, cobalt hexafluorosilicate, iron hexafluorosilicate, potassium hexafluorosilicate, nickel hexafluorosilicate, barium hexafluorosilicate, hydroxyammonium hexafluorosilicate, sodium hexafluorosilicate and calcium fluorosilicate. The preparation of sodium hexafluorosilicate is described in U.S. Pat. Nos. 4,161,511 and 4,160,012; the disclosures of which are herein incorporated by reference in their entirety. Of particular interest in many embodiments are solutions of sodium silicate, where the manufacture of dry sodium silicate ($Na_2SiO_3$, $Na_6Si_2O_7$ and $Na_2Si_3O_7$) is described in Faith, Keyes & Clark's INDUSTRIAL CHEMICALS (1975) pp 755-761.

In certain embodiments, the setting fluid may further include an amount of phosphate ion, as described in U.S. Application Publication No. 20040250730; the disclosure of which is herein incorporated by reference in its entirety. For example, the concentration of phosphate ion in the setting fluid may vary, but may be 0.01 mol/L or greater, such 0.02 mol/L or greater and including 0.025 mol/L or greater, where the concentration may range from 0.01 to 0.5, such as from 0.01 to 0.25, including from 0.02 to 0.2 mol/L. The desired phosphate concentration may be provided using any convenient phosphate source, such as a non-calcium-containing salt of phosphoric acid that is sufficiently soluble, e.g., $Na_3PO_4$, $Na_2HPO_4$, or $NaH_2PO_4$. Salts of other cations such as $K^+$, $NH_4^+$, etc., may also be employed.

Aspects of the invention include the presence of cyclodextrin in the composition prepared from the dry reactants and the setting fluid. Depending on the desired format, the cyclodextrin may be present in the dry reactants or in the setting fluid. By cyclodextrin is meant a cyclic oligosaccharide or mixture of cyclic oligosaccharides, composed of 5 or more α-D-glucopyranoside units that exhibit a 1→4 linkage. Cyclodextrins of interest include α-cyclodextrin, β-cyclodextrin and γ-cyclodextrin. The amount of cyclodextrin that is present in either the liquid or dry components may vary, depending on the amount that is desired in the flowable composition produced therefrom. In some instances, the amount of cyclodextrin that is desired in the flowable composition produced upon combination of the dry reactants and setting fluid ranges from 0.01 to 10% (w/w), such as 0.05 to 2.0% (w/w). In some instances where the cyclodextrin is present in the dry reactant component, the amount of cyclodextrin that is present in the dry reactant component ranges from 0.01 to 10% by weight, such as 0.05 to 2.0% by weight.

In certain embodiments, the cements may further include an amount of an emulsifying agent, as described in U.S. application Ser. No. 11/134,051 (published as US 2005-0260279); the disclosure of which is herein incorporated by reference in its entirety. Emulsifying agents of interest include, but are not limited to: polyoxyethylene or polyoxypropylene polymers or copolymers thereof, such as polyethylene glycol and polypropylene glycol; nonionic cellulose ethers such as methylcellulose, ethylcellulose, hydroxymethylcellulose, hydroxyethylcellulose, carboxymethylcellulose, carboxyethylcellulose and hydroxypropylcellulose; additional celluloses, such as carboxymethylcellulose sodium, carboxymethylcellulose calcium, carboxymethylstarch; polysaccharides produced by microbial fermentation, such as yeast glucans, xanthan gum, β-1,3-glucans (which may be straight-chained or branched; e.g. curdlan, paramylum, pachyman, scleroglucan, laminaran); other natural polymers, e.g., gum arabic, guar gum, carrageenin, gum tragacanth, pectin, starch, gelatin, casein, dextrin, cellulose; polyacrylamide; polyvinyl alcohol; starch; starch phosphate; sodium alginate and propylene glycol alginate; gelatin; amino-containing acrylic acid copolymers and quaternization products derived therefrom; and the like.

In certain embodiments, the emulsifying agent is a cellulose ether, particularly a nonionic cellulose ether, such as carboxymethylcellulose. Carboxymethylcellulose is available from a variety of commercial sources, including but limited to, Sigma, Hercules, Fluka and Noviant. In certain embodiments, the average molecular weight of the cellulose ether is 1000 daltons or higher, such as 5000 daltons or higher, where the average molecular weight may be as high as 10,000 daltons or higher, e.g., 50,000 daltons or higher, 100,000 daltons or higher, and ranges in certain embodiments from 5,000 to 100,000 daltons, such as from 10,000 to 50,000 daltons.

The proportion of the emulsifying agent in the cement in certain embodiments ranges from 0.01 to 10% (w/w), such as from 0.05 to 2.0% (w/w).

When employed, the emulsifying agent may be included in one or both of the above liquid and dry reactant components.

In certain embodiments, the cement may further include a contrast or imaging agent, where the contrast agent may be present in one or both of the liquid and dry components, or separate therefrom until combination of all of the components to produce the flowable composition. Contrast agents of interest include, but are not limited to: the water soluble contrast agents described in U.S. Pat. No. 7,306,786, the disclosure of which is herein incorporated by reference in its entirety; and the barium apatite contrast agents described in U.S. application Ser. No. 10/851,766 (Published as US20050257714), the disclosure of which is herein incorporated by reference in its entirety.

One or both of the above liquid and dry reactant components may include an active agent that modulates the properties of the product into which the flowable composition prepared by the subject method sets. Such additional ingredients or agents include, but are not limited to: organic polymers, e.g., proteins, including bone associated proteins which impart a number of properties, such as enhancing resorption, angiogenesis, cell entry and proliferation, mineralization, bone formation, growth of osteoclasts and/or osteoblasts, and the like, where specific proteins of interest include, but are not limited to: osteonectin, bone sialoproteins (Bsp), α-2HS-glycoproteins, bone Gla-protein (Bgp), matrix Gla-protein, bone phosphoglycoprotein, bone phosphoprotein, bone proteoglycan, protolipids, bone morphogenic protein, cartilage induction factor, platelet derived growth factor, skeletal growth factor, and the like; particulate extenders; inorganic water soluble salts, e.g., NaCl, calcium sulfate; sugars, e.g., sucrose, fructose and glucose; pharmaceutically active agents, e.g., antibiotics; and the like. Additional active agents of interest include osteoclast induction agents, e.g., RANKL, as described in U.S. Pat. No. 7,252,833, the disclosure of which is herein incorporated by reference in its entirety.

To prepare flowable compositions from the dry reactants and setting fluids, suitable amounts of the dry reactants and the setting fluid are combined to produce a settable or flowable composition. In other words, the ratio of the dry reactants to setting fluid (i.e. the liquid to solids ratio) is selected to provide for a "settable" or "flowable" composition, where by "settable" or "flowable" composition is meant a composition that goes from a first non-solid (and also non-gaseous) state to a second, solid state after setting. In some embodiments, the liquid to solids ratio is chosen to provide for a flowable composition that has a viscosity ranging from that of milk to that of modeling clay. As such, the liquids to solids ratio employed in the subject methods may range from 0.2 to 1.0, such as from 0.3 to 0.6. Of interest in certain embodiments are methods that produce a paste composition, where the liquid to solids ratio employed in such methods may range from 0.25 to 0.5, such as from 0.3 to 0.45.

As mentioned above, the requisite amounts of dry reactants and setting fluid are combined under conditions sufficient to produce the flowable product composition. As such, the dry and liquid components may be combined under agitation or mixing conditions, such that a homogenous composition is produced from the dry and liquid components. Mixing may be accomplished using any convenient means, including manual mixing as described in U.S. Pat. No. 6,005,162 and automated mixing as described in WO 98/28068, the disclosures of which are herein incorporated by reference in their entirety. Also of interest is the device disclosed in U.S. Pat. No. 5,980,482, the disclosure of which is herein incorporated by reference in its entirety. Of interest in certain embodiments are the storage/mixing elements disclosed in U.S. Pat. Nos. 6,375,935 and 6,719,993; as well as U.S. application Ser. No. 10/462,075 (Published as US20040250730); U.S. Pat. No. 7,306,786; U.S. Pat. No. 7,252,833; U.S. application Ser. No. 10/851,766 (Published as US20050257714); U.S. Pat. No. 7,261,717; U.S. Pat. No. 7,252,672; and U.S. Pat. No. 7,252,841; the disclosures of which are herein incorporated by reference in their entirety.

The temperature of the environment in which combination or mixing of the dry and liquid components takes place is sufficient to provide for a product that has desired setting and strength characteristics, and may range from 0 to 50° C., such as from 20 to 30° C. Mixing takes place for a period of time sufficient for a flowable composition to be produced, and may take place for a period of time ranging from 15 to 120 seconds, such as from 15 to 100 seconds and including from 15 to 60 seconds, e.g., 15 to 50 seconds, 15 to 30 seconds, etc.

The above-described protocols result in the production of a flowable composition that is capable of setting into a calcium phosphate mineral product, as described in greater detail below.

The flowable compositions produced by the above-described methods are compositions that set into a biologically compatible, and often resorbable and/or remodelable, product, where the product is characterized by including calcium phosphate molecules not present in the initial reactants, i.e., that are the product of a chemical reaction among the initial reactants.

The term flowable is meant to include paste-like compositions, as well as more liquid compositions. As such, the viscosity time of the subject flowable compositions, defined as time periods under which the mixed composition injects through a standard Luer-lok fitting after mixing, typically ranges up to 10 minutes, usually up to 7 minutes, such as up to 4 minutes. Of interest in certain embodiments are paste compositions that have an injectable viscosity that injects in a time period ranging up to 5 minutes, such as up to 4 minutes. Pastes that stay paste-like for longer period may be displaced by bleeding bone once implanted into the body, which create a blood interface between the cement and the bone prior to the cement hardening.

The compositions produced by the subject invention set into calcium phosphate mineral containing products. By "calcium phosphate mineral containing" product is meant a solid product that includes one or more, usually primarily one, calcium phosphate mineral. In many embodiments, the calcium phosphate mineral is one that is generally poorly crystalline, so as to be resorbable and, often, remodelable, over time when implanted into a physiologically site. The calcium to phosphate ratio in the product may vary depending on particular reactants and amounts thereof employed to produce it, but typically range from 2:1 to 1.33:1, usually from 1.8:1 to 1.5:1 and more usually from 1:7:1 to 1.6:1. Of interest in certain embodiments are apatitic products, which apatitic products have a calcium to phosphate ratio ranging from 2.0:1 to 1.33:1, including both hydroxyapatite and calcium deficient analogs thereof, including carbonate substituted hydroxyapatite (i.e. dahllite), etc. The subject paste-like composition is, in certain embodiments, one that is capable of setting into a hydroxyapatitic product, such as a carbonated hydroxyapatite, i.e. dahllite, having a carbonate substitution of from 2 to 10%, usually from 2 to 8% by weight of the final product.

The period of time required for the compositions to harden or "set" may vary. Set time is determined using the Gilmore Needle Test (ASTM C266-89), modified with the cement submerged under 37° C. physiological saline. The set times of the subject cements may range from 30 seconds to 30 minutes, and will usually range from 2 to 15 minutes and more usually from 4 to 12 minutes. In certain embodiments, the flowable composition sets in a clinically relevant period of time. By clinically relevant period of time is meant that the paste-like composition sets in less than 20 minutes, usually less than 15 minutes and often in less than 10 minutes, where the composition remains flowable for 1 minute or longer, usually 2 minutes or longer and, in many embodiments, for 5 minutes or longer following combination or mixture of the precursor liquid and dry cement components.

In some instances, the compositions rapidly set into a high strength product, as determined by the ASTM C403/C403M-06 modified test described in the experimental section below. In some instances, the compositions attain high strength rapidly, such that they may be viewed as rapid strength attainment compositions. As such, at 4 minutes the compositions of certain embodiments have a setting value of 1000 Newtons or greater, such as 1200 Newtons or greater, where the setting value may be as high as 1300 or 1400 Newtons or greater. At 6 minutes the compositions may have a setting value of 1500 Newtons or greater, such as 1700 Newtons or greater, including 1800 Newtons or greater, e.g., 1900 Newtons or greater or 2000 Newtons or greater.

The compressive strength of the product into which the flowable composition sets may vary significantly depending on the particular components employed to produce it. Of particular interest in many embodiments is a product that has a compressive strength sufficient for it to serve as at least a cancellous bone structural material. By cancellous bone structural material is meant a material that can be used as a cancellous bone substitute material as it is capable of withstanding the physiological compressive loads experienced by compressive bone under at least normal physiological conditions. As such, the subject flowable paste-like material is one that sets into a product having a compressive strength of 20 or greater, such as 40 and greater, and including 50 or greater MPa, as measured by the assay described in Morgan, E F et al., 1997, Mechanical Properties of Carbonated Apatite Bone Mineral Substitute: Strength, Fracture and Fatigue Behavior. J. Materials Science: Materials in Medicine. V. 8, pp 559-570, where the compressive strength of the final apatitic product may be as high as 60 MPa or higher. Compressive strengths can be obtained that range as high 100 to 200 MPa.

The resultant product may have a high tensile strength. Tensile strength is determined using the protocol described in the experimental section below, and where the products may exhibit a 24-hour tensile strength of 5 MPa or greater, such as 7 MPa or greater, e.g., 7.5 to 8 MPa.

In certain embodiments, the resultant product is stable in vivo for extended periods of time, by which is meant that it does not dissolve or degrade (exclusive of the remodeling activity of osteoclasts) under in vivo conditions, e.g., when implanted into a living being, for extended periods of time. In these embodiments, the resultant product may be stable for 4 months or longer, 6 months or longer, 1 year or longer, e.g., 2.5 years, 5 years, etc. In certain embodiments, the resultant product is stable in vitro when placed in an aqueous environment for extended periods of time, by which is meant that it does not dissolve or degrade in an aqueous environment, e.g., when immersed in water, for extended periods of time. In these embodiments, the resultant product may be stable for 4 months or longer, 6 months or longer, 1 year or longer, e.g., 2.5 years, 5 years, etc.

In certain embodiments of interest, the product that is produced is a composite product, which includes some unreacted particles, e.g., from the coarse particulate reactant, present in the final product. In certain of the embodiments where such a cement is implanted into an in vivo site, the unreacted particles may dissolve (e.g., via resorption) over time leaving a porous structure at the implant site, where the porous structure remains until it is remodeled. In certain embodiments, the remaining coarse particles in the composite may have a different radiopacity than the remainder of the product, e.g., where at least a portion of the coarse particles in the cement were dolomite.

In certain embodiments, the flowable paste-like composition is capable of setting in a fluid environment, such as an in vivo environment at a bone repair site. As such, the flowable paste composition can set in a wet environment, e.g., one that is filled with blood and other physiological fluids. Therefore, the site to which the flowable composition is administered during use need not be maintained in a dry state.

In certain embodiments, the subject cement compositions may be seeded with any of a variety of cells, as described in published U.S. Patent Publication No. 20020098245, the disclosure of which is herein incorporated by reference in its entirety.

In addition, in certain embodiments the compositions include demineralized bone matrix, which may be obtained typically in a lyophilized or gel form and is combined with the cement composition at some prior to implantation. A variety of demineralized bone matrixes are known to those of skill in the art and any convenient/suitable matrix composition may be employed.

In certain embodiments, the cements may include one or more collections of contrast particles (for example, for use as tracers during use of the cement), e.g., as described in U.S. Pat. No. 6,273,916 or U.S. application Ser. Nos. 10/629,31 and 10/851,766; the disclosures of which are herein incorporated by reference in their entirety.

One cement composition in which the tricalcium phosphate coarse particles of the invention find use is the composition described in PCT application serial no. PCT/US2005/026369 and published as WO/2006/014886, the disclosure of which is herein incorporated by reference.

Applications

Flowable compositions produced from cements of the invention, e.g., as described above, find use in applications where it is desired to introduce a flowable material capable of setting up into a solid calcium phosphate product into a physiological site of interest, such as in dental, craniomaxillofacial and orthopedic applications. In orthopedic applications, the cement may be prepared, as described herein, and introduced or applied to a bone repair site, such as a bone site comprising cancellous and/or cortical bone. In some instances, the site of application is a cancellous bone void that results from reducing a fracture. In these instances, the methods may include reducing a bone fracture and then applying an amount of the flowable composition to the resultant void, where the amount may be sufficient to substantially if not completely fill the void.

Orthopedic applications in which the cements prepared by the subject system find use include, but are not limited to, the treatment of fractures and/or implant augmentation, in mammalian hosts, particularly humans. In such fracture treatment methodologies, the fracture is first reduced. Following fracture reduction, a flowable structural material prepared by the subject system is introduced into the cancellous tissue in the fracture region using the delivery device described above. Specific dental, craniomaxillofacial and orthopedic indications in which the subject invention finds use include, but are not limited to, those described in U.S. Pat. No. 6,149,655, the disclosure of which is herein incorporated by reference in its entirety. In addition to these particular applications described in this U.S. Patent, the subject cement compositions also find use in applications where a sternotomy has been performed. Specifically, the subject cements find use in the closure process of a sternotomy, where the bone fragments are rejoined and wired together, and any remaining cracks are filled with the subject cement. In yet other embodiments, the subject compositions find use in drug delivery, where they are capable of acting as long lasting drug depots following administration to a physiological site. See e.g. U.S. Pat. Nos. 5,904,718 and 5,968,253; the disclosures of which are herein incorporated by reference in their entirety.

Representative applications of interest also include, but are not limited to: those described in U.S. Pat. Nos. 6,375,935 and 6,719,993; as well as U.S. application Ser. No. 10/462,075 (Published as US20040250730); U.S. Pat. No. 7,306,786; U.S. Pat. No. 7,252,833; U.S. application Ser. No. 10/851,766 (Published as US20050257714); U.S. Pat. No. 7,261,717; U.S. Pat. No. 7,252,672; and U.S. Pat. No. 7,252,841; the disclosures of which are herein incorporated by reference in their entirety.

Kits

Also provided are kits that include the subject cements, where the kits at least include a dry particulate component and a cyclodextrin, as described above. In certain embodiments, the kits further include a volume of a setting fluid, as described above. When both a dry component and setting fluid are present, the dry component and setting fluid may be present in separate containers in the kit, or some of the components may be combined into one container, such as a kit wherein the dry components are present in a first container and the liquid components are present in a second container, where the containers may or may not be present in a combined configuration, as described in U.S. Pat. No. 6,149,655, the disclosure of which is herein incorporated by reference in its entirety. In addition to the cement compositions, the subject kits may further include a number of additional reagents, e.g., cells (as described above, where the composition is to be seeded), protein reagents (as described above), and the like.

In certain embodiments, the subject cements may be kitted as described in U.S. Pat. No. 6,273,916, the disclosure of which is herein incorporated by reference in its entirety, e.g., packaged in a kit with at least two different sterilized pouches (or analogous compartments) of cement that may independently used at the same or different times, where each pouch may include the same or different cement formulation, e.g., where the cements may differ in terms of contrast characteristics.

In certain embodiments, the kits may further include mixing and/or delivery elements, e.g., mortar and pestle, spatula, etc., which elements find use in, e.g., the preparation and/or delivery of the cement composition.

In addition to above-mentioned components, the subject kits typically further include instructions for using the components of the kit to practice the subject methods. The instructional material may also be instructional material for using the cement compositions, e.g., it may provide surgical techniques and principals for a particular application in which the cement is to be employed. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Systems

Also provided are systems that find use in practicing the subject methods, as described above. The subject systems at least include dry and liquid components of a cement, as described above, and a mixing element. In certain embodiments, the systems may further include additional agents, e.g., contrast agents, active agents, etc., as described above.

The following examples are offered by way of illustration and not by way of limitation.

Experimental

I. Process of Forming Coarse Particles

| Step | Description of step |
|---|---|
| 1 | Weigh 1414.1 g ± 1.0 g DCPA and 520.2 g ± 1.0 g Calcite in a container |
| 2 | Blend on jar mill using '100' setting |
| 3 | Weigh 1395.2 g ± 1.0 g DI $H_2O$ into a beaker |
| 4 | Carefully introduce blended powder into beaker |
| 5 | Mix using blender on low setting |
| 6 | Fill tray molds with slurry to depth of ¾ inches |
| 7 | Place trays in oven at 110° C. |
| 8 | Take the trays out and let them cool to room temperature |
| 9 | Place cakes in alumina trays for firing |
| 10 | Fire the cakes at 1425° C. |
| 11 | Quench the cakes with a stainless steel rod |
| 12 | Let the quenched material cool to room temperature |

-continued

| Step | Description of step |
|---|---|
| 13 | Put the material into disc mill (3 times) at a gap setting of 254 μm in order to obtain <38 μm particle size |
| 14 | Place the <38 μm powder in the stainless steel bucket of the blender |
| 15 | Prepare sodium phosphate solution by dissolving 11.2 grams in 465 grams DI $H_2O$ |
| 16 | Add the sodium phosphate solution into the powder and mix (Formation of Hydroxyapatite) |
| 17 | Scrape the attached paste from the container |
| 18 | Dry at 140° C. overnight and cool |
| 19 | Disc Mill the powders at a gap setting of 1500 μm |
| 20 | Send the powders for pellet making (Pelletize) |
| 21 | Receive the pellets from pellet making |
| 22 | Fire the pellets at 1425° C. for 2 hours (Sintering) |
| 23 | Quench by spreading the pellets on a stainless steel tray |
| 24 | Grind the pellets in the disc mill at a gap setting of 500 μm (Start of Mechanical manipulation) |
| 25 | Sieve the disc milled powder |
| 26 | Disc mill the >212 μm powders at a gap setting of 254 μm |
| 27 | Sieve the disc milled powder |
| 28 | Disc mill the >212 μm powders at a gap setting of 254 μm |
| 29 | Sieve the disc milled powder |
| 32 | The process yields 60% particles of 38-212 μm<br>570 grams particles of 38-212 μm<br>380 grams of waste <38 μm |

Figure 1B:
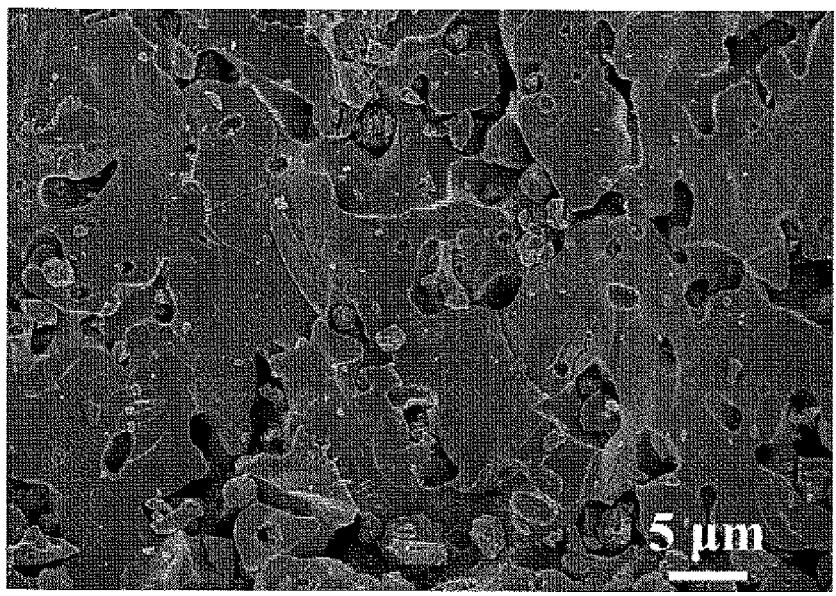
FIG. 1b shows an SEM micrograph of particles obtained that are 106-212 μm.

FIGS. 1A and 1B (9a and 9b from SKEL-027) show morphology of particles formed by the above process. FIG. 1A shows an SEM micrograph of particles obtained that are 38-106 μm. FIG. 1B shows an SEM micrograph of particles obtained that are 106-212 μm. The coarse particles are very dense and strong.

An Inductively Coupled Plasma-Atomic Emission Spectrocopy (ICP-AES) analysis of the particles is provided in Table 1, below.

TABLE 1

ICP-AES Analysis of coarse particles synthesized by different processes

| | Control | | Test | |
|---|---|---|---|---|
| Element | 38-106 μm | 106-212 μm | 38-106 μm | 106-212 μm |
| P (%) | 20.02 | 20.1 | 19.05 | 19.61 |
| K (%) | 0.01 | 0 | 0.01 | 0.01 |
| Ca (%) | 39.57 | 40 | 38.05 | 38.04 |
| Mg (%) | 0.08 | 0.08 | 0.12 | 0.12 |
| Zn (ppm) | 7.2588 | 6.4048 | 5.8 | 8.7 |
| Cu (ppm) | 0 | 0 | 1.77 | 1.39 |
| Mn (ppm) | 6.1219 | 6.9635 | 6.49 | 10.37 |
| Fe (ppm) | 129.63 | 88.889 | 136.36 | 157.25 |
| S (%) | 0.07 | 0.01 | 0.01 | 0.01 |
| Na (ppm) | 26.51 | 27.65 | 1722 | 1798 |
| B (ppm) | 5.399 | 6.351 | 10.11 | 11.18 |
| Al (ppm) | 84.36 | 56.24 | 159.95 | 227.9 |
| N (%) | 0 | 0 | 0 | 0 |
| Si (ppm) | 149.5 | 152 | 117.5 | 97 |
| Zr (ppm) | 24 | 13.5 | 25 | 11.5 |

II. Process of Forming Fine Calcium Phosphate Particles

The fine or 2 μm α-TCP is prepared as follows:
a. Monetite ($CaHPO_4$) is combined with calcite ($CaCO_3$) in a ball mill
b. Water is added to this mixture and form a slurry
c. The slurry is placed into molds to make wet cakes
d. The cakes are fired 1425° C. for 1 hour followed by quenching
e. Ball mill and sieve the powder to obtain fractions of <38 μm α-TCP, 38-106 μm α-TCP, and 106-212 μm α-TCP
f. Jet mill <38 μm α-TCP fraction to obtain 2 μm α-TCP
The mean particle size is in the range of 2-3 μm.

III. Test Formulations
A. Formulation #1

| Material | Range | Average |
|---|---|---|
| Alpha-cyclodextrin = | 0.023-0.027 grams | 0.025 grams |
| SPMA = | 0.104-0.114 grams | 0.109 grams |
| 106-212 μm α-TCP* = | 3.070-3.110 grams | 3.090 grams |
| 2 μm α-TCP = | 6.470-6.490 grams | 6.480 grams |
| Total average powder weight = | | 9.704 grams |
| Liquid (dil. Na-silicate soln.) = | 2.990-3.010 grams | 3.00 grams |

Liquid to powder ratio = 0.31

B. Formulation #2

| Material | Range | Average |
|---|---|---|
| Alpha-cyclodextrin = | 0.023-0.027 grams | 0.025 grams |
| CMC = | 0.047-0.049 grams | 0.048 grams |
| SPMA = | 0.068-0.078 grams | 0.073 grams |
| 38-106 μm α-TCP* = | 1.506-1.526 grams | 1.516 grams |
| 106-212 μm α-TCP* = | 1.506-1.526 grams | 1.516 grams |
| 2 μm α-TCP = | 6.060-6.080 grams | 6.070 grams |
| Total average powder weight = | | 9.248 grams |
| Liquid (dil. Na-silicate soln.) = | 3.30-3.320 grams | 3.31 grams |

Liquid to powder ratio = 0.36

III. Control Formulations
A. Control Formulation #1

| Material | Range | Average |
|---|---|---|
| SPMA = | 0.104-0.114 grams | 0.109 grams |
| 106-212 μm α-TCP* = | 3.070-3.110 grams | 3.090 grams |
| 2 μm α-TCP = | 6.470-6.490 grams | 6.480 grams |
| Total average powder weight = | | 9.679 grams |
| Liquid (dil. Na-silicate soln.) = | 2.990-3.010 grams | 3.00 grams |

Liquid to powder ratio = 0.38

B. Control Formulation #2

| Material | Range | Average |
|---|---|---|
| CMC = | 0.047-0.049 grams | 0.048 grams |
| SPMA = | 0.068-0.078 grams | 0.073 grams |
| 38-106 μm α-TCP* = | 1.506-1.526 grams | 1.516 grams |
| 106-212 μm α-TCP* = | 1.506-1.526 grams | 1.516 grams |
| 2 μm α-TCP = | 6.060-6.080 grams | 6.070 grams |
| Total average powder weight = | | 9.223 grams |
| Liquid (dil. Na-silicate soln.) = | 3.30-3.320 grams | 3.31 grams |

Liquid to powder ratio = 0.42

C. Mixing

For both formulations, the powder and liquid are mixed using a mortar and pestle to produce paste which is then allowed to set and tested as described above.

IV. Setting Strength
A. Methods

A modification of the standard setting test described in ASTM C403/C403M-06 is employed, in which the load required to drive needles a prescribed distance into concrete or a similar setting material is measured. The modification involves a needle with a tip configuration similar to that used in ASTM C266-07. A modified high load indentor (7 mm in diameter) is attached to Instron material testing machine with a maximum load of 5000 N. The needle is pushed 1.25 mm at a rate of 15.2 mm/s into the sample cured at 32±0.5° C. and 100% RH. No spring load average is calculated or used in later calculations (the high load indentor test fixture does not use a spring).

B. Results

An indentation load in excess of 3.5 MPa (135 Newton) has been determined as the time of initial setting according to the standard of ASTM C403/C403M-06.

| | | Control | Test |
|---|---|---|---|
| Form #1 | 4 min Setting Strength | 600N | 1700N |
| | 6 min Setting Strength | 1000N | 2200N |
| Form #2 | 4 min Setting Strength | 500N | 1400N |
| | 6 min Setting Strength | 900N | 1900N |

As can be seen from the above results, inclusion of alpha cyclodextrin significantly increases the setting strength as compared to the control.

V. Tensile Strength
A. Methods

The testing was conducted using an Instron mechanical testing system (Canton, Mass.). The test specimens were circular rings of 0.5" I.D. and 0.3" thickness that were filled with the cement using a spatula. The filled molds were placed into a phosphate buffered saline bath maintained at 37° C. and allowed to cure for 24 hours. Samples were then removed from the unit, placed on a steel platen and crushed at a cross head speed of 0.1 inches/minute. Ultimate tensile stress was calculated using the following equation:

$$\text{Equation of tensile stress: } \sigma = 2P/\pi Dt$$

where:
P=ultimate compressive load, Newtons
D=sample diameter, millimeters
t=sample thickness, millimeters.

B. Results

| | | Control | Test |
|---|---|---|---|
| Form #1 | 24 hr Tensile Strength | 4.5 MPa | 8 MPa |
| Form #2 | 24 hr Tensile Strength | 4.3 MPa | 7.5 MPa |

As can be seen from the above results, inclusion of alpha cyclodextrin significantly increases the tensile strength as compared to the control.

VI. Compressive Strength
A. Methods

The compressive strength test is a modification of ASTM F 451. The primary difference from the ASTM method is that pressurization of the void filler specimens is not required. Additional modifications to the test involve curing the bone void filler specimens for 24 hours in a 37° C. phosphate buffered saline environment at pH=7.4 and sanding the ends of the specimens before removing them from the mold for testing. Each specimen is placed between the loading platens of the mechanical testing system. Specimens are loaded along the longitudinal axis at displacement rate of 0.1 in./min until failure. Load, displacement, and time are recorded continuously at a sampling rate of 10 Hz.

B. Results

The compressive strength for both test formulation 1 and 2 above was found to be 55 MPa.

All publications and patent applications mentioned in this specification are herein incorporated by reference to the same extent as if each individual publication or patent application was specifically and individually indicated to be incorporated by reference.

The invention now being fully described, it will be apparent to one of skill in the art that many changes and modifications can be made thereto without departing from the spirit and scope of the appended claims.

What is claimed is:

1. A kit comprising:
   (a) a dry reactant component comprising:
      (i) a first particulate tricalcium phosphate reactant having a mean particle size of 8 μm or less; and
      (ii) a second particulate tricalcium phosphate reactant having a mean particle size of 10 μm or greater, wherein the second particulate tricalcium phosphate reactant comprises tricalcium phosphate particles that range in size from 30 to 250 μm and comprise sodium in an amount ranging from 1500 to 2500 ppm;
   (b) a cyclodextrin; and
   (c) a setting fluid.

2. The kit according to claim 1, wherein the cyclodextrin is α-cyclodextrin.

3. The kit according to claim 1, wherein the setting fluid is a solution of a soluble silicate.

* * * * *